United States Patent [19]
Toomes

[11] Patent Number: 5,830,239
[45] Date of Patent: Nov. 3, 1998

[54] NATURAL TISSUE HEART VALVE FIXATION APPARATUS AND METHOD

[75] Inventor: Christopher G. Toomes, Orange, Calif.

[73] Assignee: Medtronic, Inc., Minneapolis, Minn.

[21] Appl. No.: 559,781

[22] Filed: Nov. 15, 1995

[51] Int. Cl.⁶ .......................... A61L 17/00; A63B 51/02; D01C 3/00; A61F 2/24
[52] U.S. Cl. ................ 8/94.11; 623/2; 623/11; 623/12
[58] Field of Search .................. 623/2, 11, 12; 8/94.11

[56] References Cited

U.S. PATENT DOCUMENTS

| | | | |
|---|---|---|---|
| 3,966,401 | 6/1976 | Hancock et al. | 8/94.11 |
| 4,050,893 | 9/1977 | Hancock et al. | 8/94.11 |
| 4,090,878 | 5/1978 | Hancock et al. | 69/29 |
| 4,247,292 | 1/1981 | Angell | 8/94.11 |
| 4,350,492 | 9/1982 | Wright et al. | 8/94.11 |
| 4,372,743 | 2/1983 | Lane | 8/94.11 |
| 4,443,895 | 4/1984 | Lane | 3/1.5 |
| 4,624,822 | 11/1986 | Arru et al. | 264/544 |
| 4,800,603 | 1/1989 | Jaffe | 8/94.11 |
| 5,279,612 | 1/1994 | Eberhardt | 8/94.11 |
| 5,549,666 | 8/1996 | Hata et al. | 623/2 |

FOREIGN PATENT DOCUMENTS

| | | |
|---|---|---|
| 1228203 | 10/1987 | Canada . |
| 0165622 | 12/1985 | European Pat. Off. . |
| 0402036 | 12/1990 | European Pat. Off. . |
| 0402176 | 12/1990 | European Pat. Off. . |
| 1510163 | 5/1978 | United Kingdom . |
| 2169386 | 7/1986 | United Kingdom . |
| 9014804 | 12/1990 | WIPO . |

OTHER PUBLICATIONS

"Hydrodynamic Function of Second Generation Porcine Bioprosthetic Heart Valves" by Maya Butterfield, M.Sc, John Fisher, Ph.D., John Nigel Kearney, Ph.D., and Gwilym Alban Davies, F.R.C.S., *Journal of Cardiac Surgery*, 6, No. 4, Dec. 1991, pp. 490–498.

"Improved Leaflet Geometry and Function in Procine Bioprosthetic Heart Valves: The Next Generation" by M. Butterfield, J. Fisher, and G.A. Davies, *Fourth World Biomaterials Congress*, Apr. 24–28,1992, p.82.

"The Stentless Bioprosthesis: Surgical Challenges and Implications for Long–Term Durability" by B.G. Baratt–Boyles, G.W. Christie, and P.J. Raudikivi, *Eur. J. Cardio–Thoracic Surg.*, (1992) 6 [Suppl.1] pp. 39–43.

*Primary Examiner*—Paul B. Prebilic
*Attorney, Agent, or Firm*—Harold R. Patton; Peter Forrest; Curtis D. Kinghorn

[57] ABSTRACT

An apparatus and a method for fixing a heart valve is disclosed that produces a differential pressure across the outflow section of the heart valve to the exterior of the valve that may be made relatively large while the differential pressure across the valve leaflets is small or zero. The invention comprises attaching the outflow section of a heart valve to a source of pressurized fluid; placing a small tube through the leaflets and plugging the inflow section. The tube is preferably attached to a cannula plug that plugs the inflow section of the valve. The tube has a fluid inlet near the connection point of the tube to the cannula plug to allow fluid around the connection point to enter the tube. The tube opens at its opposite end to form a fluid channel from a point near the connection of the cannula plug to the tube through the opposite end of the tube. The tube allows fluid in the outflow section to move across the leaflets to the inflow section. Fluid that enters the inflow section will be at the same fluid pressure as the fluid that is in the outflow section.

19 Claims, 4 Drawing Sheets

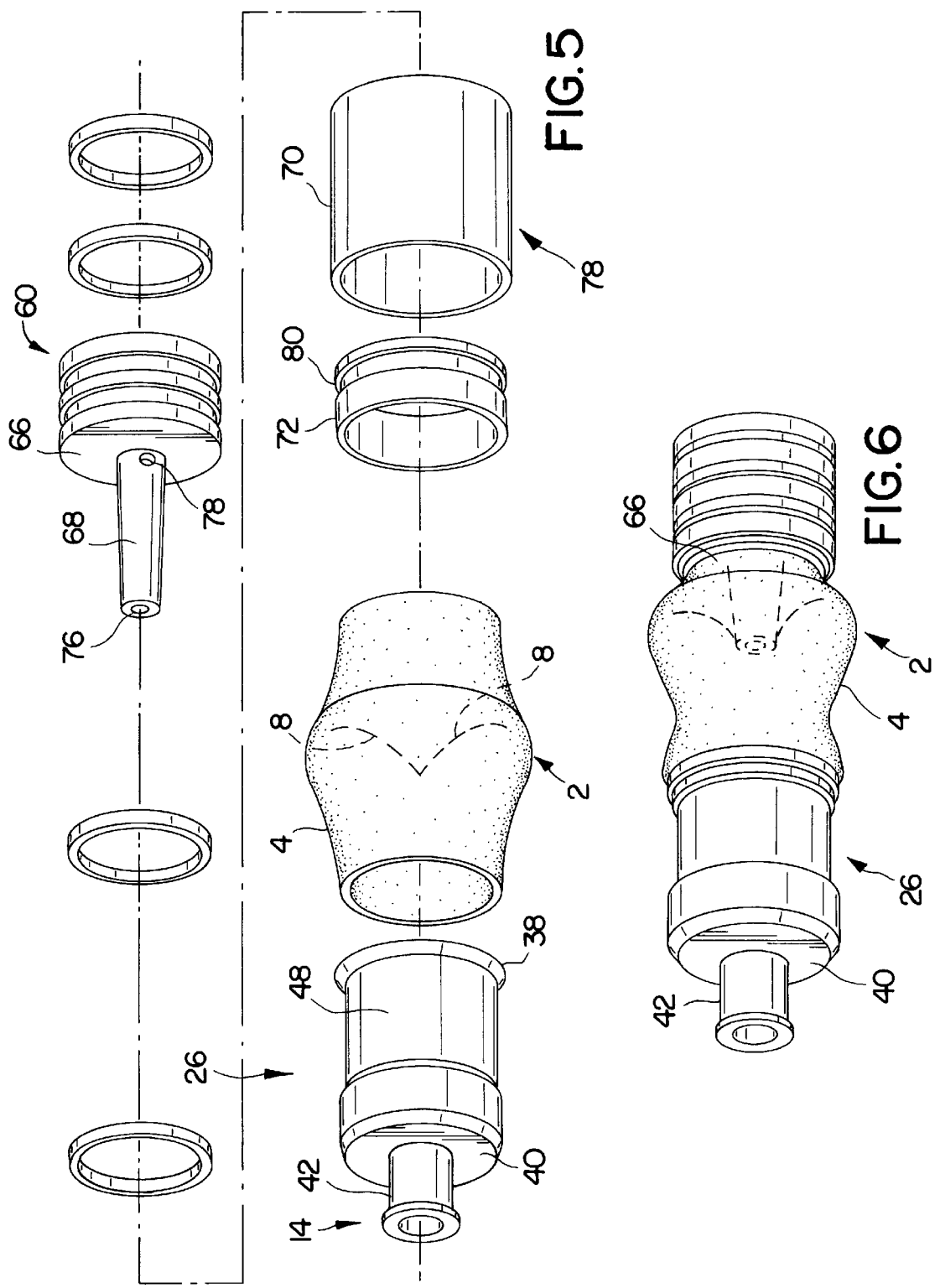

NATURAL TISSUE HEART VALVE FIXATION APPARATUS AND METHOD

BACKGROUND OF THE INVENTION

1. Field of the Invention

This invention relates to a device and method for fixing natural tissue heart valves.

2. Description of Related Art

Animal heart valves, such as porcine heart valves, are commonly used as implants in humans to replace natural human heart valves. Before the animal heart valve can be used as an implant, it must undergo processing to make it suitable for human use. One important step in the processing of animal heart valves is fixation, i.e., stabilizing the tissue against degradation.

A natural tissue animal or human heart valve is shown in FIGS. 1 and 2 generally labeled 2. Valve 2 includes a tubular wall 4 defining a passage 6 and valve leaflets 8 dividing the tubular wall 4 into an inflow section 10 leading to the leaflets 8 and an outflow section 12 leading away from the leaflets 8. Leaflets 8 open to allow flow from the inflow section 10 to the outflow section 12 in response to a differential pressure across leaflets 8. This differential pressure across leaflets 8 tends to force leaflets 8 toward the outflow section 12.

After harvesting valve 2, the circumferential dimensions of the tubular wall 4 of heart valve 2 reduce as a result of the valve 2 going to a relaxed, i.e., unpressurized state. During the fixing process, outflow section 12, which in the case of an aortic valve 2 is the aortic root, must be expanded radially outwardly to near its original dimensions, i.e., to a size compatible with its natural physiological state. This prevents outflow section 12 from shrinking or partially collapsing radially inwardly after the fixing process. To expand outflow section 12 as desired, fluid pressure is applied across outflow section 12 in a radial outward direction as indicated by the arrow labeled A in FIG. 2. The radially outward pressure on outflow section 12 is sufficient to expand outflow section 12 to the desired expansion during a suitable time period.

Although the desired radially outward pressure for this task may vary over a wide range, the pressure has been found to be most effective in the range of from about 20 mm Hg to about 120 mm Hg. relative to the pressure outside of outflow section 12. This radially outward pressure differential is generally achieved by surrounding valve 2 with a fluid at a relatively low pressure and putting fluid inside tubular wall 4 at a relatively high pressure.

Another consideration in the fixation process is the differential fluid pressure across valve leaflets 8. Here, differential pressure across leaflets 8 means the difference in fluid pressure in the inflow section 10 and the outflow section 12. The reported desired differential pressure across leaflets 8 varies widely depending upon the school of thought of the scientists involved and other factors. However, it is generally believed desirable to fix valve leaflets 8 with low or zero differential fluid pressure acting across leaflets 8. For example, the differential fluid pressure acting across leaflets 8 in a direction from inflow section 10 to outflow section 12 is preferably from about 0 mm Hg to about 4 mm Hg.

A problem has been that the leaflets 8 tend to close during the fixing process so that fluid under pressure in the outflow section 12 cannot move across the closed leaflets 8 to the inflow section 10. Consequently, the relatively high fluid pressures in tubular wall 4 required for expanding outflow section 12 are not transferred across leaflets 8 to inflow section 10. As a result, a greater pressure differential is formed across leaflets 8 than is desirable. If leaflets 8 are fixed in this condition, the collagen waveforms of leaflets 8 tend to stretch to the extent that leaflets 8 become undesirably stiff. On the other hand, if low pressure is applied to the fluid in tubular wall 4 so that, at worst, a low pressure differential occurs across leaflets 8, the low pressure in tubular wall 4 is insufficient to expand outflow section 12 as desired.

This problem has been solved, as described in co-pending U.S. patent application Ser. No. 08/129,626, by subjecting outflow section 12 and leaflets 8 to different independently selected differential fluid pressures. Each of these differential fluid pressures is independently selected to achieve the desired expansion of outflow section 12 and the desired low pressure differential across leaflets 8. This method reduces the distortion of a natural tissue heart valve 2 that was inherent in previously used fixation techniques.

Specifically, using this differential pressure technique disclosed in the '626 application and referring to FIG. 3, natural tissue heart valves have been fixed by subjecting the valve 2 to a fixative fluid at a first fluid pressure in tubular wall 4, a second lower fluid pressure outside tubular wall 4 and a differential pressure across leaflets 8 that is relatively small, approaching zero. This fixative fluid could be any fluid, either liquid or gas, which is suitable for fixing a natural tissue heart valve 2. A glutaraldehyde solution is presently preferred.

A first fluid pressure is applied inside tubular wall 4 to enlarge the wall of the outflow section 12. A second fluid pressure is applied inside tubular wall 4 to inflow section 10. The second fluid pressure may be, but need not be, the same as the first fluid pressure. In a preferred practice of the method, valve 2 is immersed in a bath of glutaraldehyde at atmospheric pressure. The pressure difference between the fluid inside and outside valve 2 causes a pressure differential that acts outwardly on outflow section 12. The first fluid pressure is chosen to enlarge the wall of outflow section 12. For many applications, the first fluid pressure is preferably in the range of from about 20 mm Hg to about 82 mm Hg. Specifically, for a porcine aortic heart valve, the first fluid pressure is preferably in the range of from about 20 mm Hg to about 50 mm Hg, with 40 mm Hg being considered optimum.

A fluid pressure differential acts across leaflets 8. This fluid pressure differential is preferably low and in the range of from about 0 mm Hg to 4 mm Hg. A differential pressure of substantially 0 mm Hg is considered optimum.

The method also provides for varying of the pressures during fixation. For example, the fluid pressure differential across leaflets 8 may be periodically varied to cause opening and closing of the valve leaflets 8. This results in some of the fixative fluid flowing through the valve leaflets 8.

Although the method may be carried out in different ways, in one preferred technique, fixative fluid under pressure is supplied to the inflow section 10 and outflow section 12 through separate openings in these sections. Thus, the inflow section 10 and outflow section 12 are coupled to fixative fluid under pressure.

As stated above, valve 2 is preferably immersed in a bath of fixative solution. This bath has fluid pressure approximately equal to atmospheric pressure. In this configuration, the fixative fluid that is in inflow section 10 and outflow section 12 is at a pressure greater than the atmospheric pressure of the bath acting on the outside of the valve 2. This provides the desired differential fluid pressure acting outwardly across the tubular wall 4 of the outflow section 12.

The pressure differential of the fixative fluid in inflow section 10 relative to the pressure of the fixative fluid in outflow section 12 creates the desired differential fluid pressure across leaflets 8. For example, by providing fixative fluid at 40 mm Hg in both inflow section 10 and outflow section 12, the differential fluid pressure acting across outflow section 12 to the exterior of valve 2 is about 40 mm Hg, and the differential fluid pressure acting across leaflets 8 is about 0 mm Hg.

Inflow section 10 and outflow section 12 may be coupled to the same or separate sources of fixative fluid under pressure. In one apparatus used to carry out the method, inflow section 10 and outflow section 12 are coupled to different sources of fixative fluid, respectively. In another apparatus, inflow section 10 and outflow section 12 are both connected to the same source of fixative fluid. In this last embodiment, the fluid pressure in both inflow section 10 and outflow section 12 will be the same, namely, the pressure provided by the source of fixative fluid.

In either embodiment, both the inflow section 10 and the outflow section 12 are connected to a source of fixative fluid; in one embodiment the sources are different and in another embodiment the sources are the same. It is necessary to have connectors and tubing to connect valve 2 to the source or sources of fixative fluid and to transport the fixative fluid to and from valve 2. As a result, both inflow section 10 and outflow section 12 have at least one corresponding connector and connecting tubing.

FIG. 3 shows, in part, an embodiment of the connectors that connect both inflow and outflow sections 10, 12 to the source of fluid. An inflow connector 14 is attached to inflow section 10. Inflow connector 14 is substantially cylindrical and is comprised of a body 16, a cylindrical protrusion 18, a rigid annular band 20 and an inlet port 22. Inflow section 10 is attached to inflow connector 14 by folding a portion 23 of inflow section 10 over annular band 20 so that a cross-section of inflow section 10, band 20 and inflow section 10 is formed radially from the center of inflow section 10. Connector 14 is coupled to a source $S_2$ of fixative fluid by any suitable manner. This coupling may be done, but is not limited to being done, by clamping or gluing tubing to a source of fixative fluid $S_2$ at one end and to the inflow connector 14 at the other end.

Cylindrical protrusion 18 extends distally from body 16. Cylindrical protrusion 18 is placed over the outer layer of inflow section 10 that is outside of annular band 20. A securing compression ring 24 wraps around cylindrical protrusion 18 and secures inflow section 10 to inflow connector 14.

An outflow connector 26 is attached to outflow section 12. Outflow connector 26 is preferably tubular and includes a body 28, a cylindrical protrusion 30 and an inlet port 32. Connector 26 cooperates with the outflow section 12 to provide an outflow chamber 34. Connector 26 is preferably constructed of a rigid polymeric material, such as acetalphomopolymer or thermoplastic.

Protrusion 30 has a smooth, external peripheral surface 36 and terminates in an annular distal rib 38. Body 28 has a proximal shoulder 40.

Inlet port 32 is formed by a reduced diameter neck 42 that terminates proximally in a proximal rib 44. Neck 42 has a bore 46 extending axially therethrough. Connector 26 is coupled to a source $S_1$ of fixative fluid by any suitable manner. This coupling may be done, but is not limited to being done, by clamping or gluing tubing to a source of fixative fluid $S_1$ at one end and to the inlet port 32 at the other end.

Cylindrical protrusion 30 encloses a chamber 48. An end wall 50 defines a proximal end of chamber 48. An inlet opening 52 extends through end wall 50 to provide fluid communication between chamber 48 and bore 46. Chamber 48 and bore 46 allow inlet port 32 to be in fluid communication with outlet section 12. Both inlet ports 22, 32 are connected to sources of fixative fluid under pressure.

Because protrusion 30 has a smooth peripheral surface 36, connector 26 can be inserted to virtually any desired depth into outflow section 12. A conventional releasable clamping band 54 is applied around tubular wall 4 just proximal to rib 38 to clamp tubular wall 4 to the connector 26. This variable depth of insertion feature varies the length of the overall assembly shown in FIG. 3 to facilitate connecting this assembly to a source of fixative fluid.

The proximal end of outflow section 12 is placed over the distal end of cylindrical protrusion 30 including rib 38. Clamping band 54 is placed over the proximal end of outflow section 12 that extends over the distal end of cylindrical protrusion 30. Band 54 secures the proximal end of outflow section 12 in contact with the distal end of cylindrical protrusion 30.

As a practical matter, fixtures support connectors 14 and 26 so that when valve 2 is immersed in the fixative solution bath, as described above, valve 2 will be supported in the fixative solution. Inlet ports 22 and 32 are physically placed through the walls of manifolds 56, 58 (FIG. 4) so that connectors 14, 26 are in fluid communication with the interior of manifolds 56, 58. Manifolds 56, 58 themselves are rigidly supported in order to support the valve 2 during the fixing process. Manifolds 56,58 are connected to sources of fixative fluid, $S_1$ and $S_2$, respectively, under pressure.

With this arrangement, fixative fluid under pressure flows through inlet port 22 through inlet connector 14 into inflow section 10 and through inlet port 32 through outflow connector 26 into outflow section 12. This configuration requires a duplicity of connectors, fixtures and connecting tubing. This duplicity of connectors, fixtures and connecting tubing adds cost and complexity to the valve fixing operation. In addition, the added number of connectors, fixtures and connecting tubing increases the possibility of part failure and leakage. These are problems to be avoided.

A further problem with this method for fixing valves is that the method requires a large amount of human manipulation and manual labor. In particular, several of the steps in the process require adjusting or "tuning" of the apparatus. As a result, the human factor has been found to have a large influence on the quality, and subsequently the yield, of the process.

Some examples of the adjustment steps required in the process include attaching valve 2 to connectors 14, 26 so that connectors 14, 26 will be correctly supported by manifolds 56, 58. Because valve 2 itself may have a variable length, connectors 14, 26 have to be precisely adjusted to avoid stretching or compressing valve 2 while valve 2 is held in place by manifolds 56, 58 during the fixing process.

However, the section of valve 2 being fixed is a portion of the aorta that is normally arch shaped. In practice, approximately 30 mm of the aortic arch is fixed during the fixing process. The act of fixing this section of the aorta and valve 2 involve stretching the aorta between manifolds 56, 58. This results in the aorta being fixed in the unnatural straight shape instead of the natural arch shape. It is difficult, if not impossible, to adjust the connection of this portion of the aorta to manifolds 56, 58 so that no strain is placed on the aorta.

Finally, after applying hydrostatic pressure to the assembly, the system must be bled of air trapped in the valve 2. On a large scale, this is a lengthy process.

SUMMARY OF THE INVENTION

The invention comprises an apparatus and a method for fixing a heart valve so that the differential pressure across the outflow section of the heart valve to the exterior of the valve may be made relatively large while the differential pressure across the valve leaflets is small or zero. In particular, the invention comprises attaching the outflow section of a heart valve to a source of pressurized fluid and plugging the inflow section. In order to equalize the fluid pressure on the inflow and outflow side of the leaflets, especially during the initial stages of fixing, a small tube is placed through the leaflets so that fluid pressure on one side of the leaflets is passed to the other side of the leaflets. The tube or cannula is preferably attached to a plug that plugs the inflow section of the valve.

In use, a cannula plug is placed in the inflow section of the heart valve. The plug is secured to the inflow section through a fluid tight seal. A tube extends from the cannula plug into the inflow section. The tube has a fluid inlet near the connection point of the tube to the cannula plug so that fluid around the connection point may enter the tube. The tube opens at its end opposite the cannula plug to form a fluid channel from a point near the connection of the cannula plug to the tube through the end of the tube opposite the cannula plug.

The outflow section is connected to a source of fluid that will deliver fluid at a desired pressure to the outflow section. When fluid under pressure is delivered to the outflow section, the fluid will contact the leaflets. The contact of fluid to the leaflets tends to cause the leaflets to close, thereby preventing fluid from moving to the inflow section. If this condition were to persist, there would be a large fluid pressure differential across the leaflets. However, the tube, which extends through the leaflets, allows fluid in the outflow section to move across the leaflets to the inflow section. Fluid that enters the inflow section will be at the same fluid pressure as the fluid that is in the outflow section. As a result, the fluid pressure differential across the leaflets will be small or zero.

With the present invention, the pressure differential across the tubular wall will be the difference in pressure between the fluid in the valve and atmospheric pressure. This pressure difference can be made quite large while still preserving the near zero pressure differential across the leaflets. As a result, the outflow section of the heart valve can be made to expand as desired.

Although the valve has been described as being immersed in fixing fluid that is at atmospheric pressure, the valve may be immersed in fluid that is at pressures other than atmospheric pressure. In addition, the valve may be immersed in fluids other than fixing fluids.

It is an object of the invention to provide a method and apparatus for fixing a natural tissue heart valve that reduces the number and complexity of components from previously know methods and apparatuses.

It is another object of the invention to provide a method and apparatus for fixing a natural tissue heart valve that allows the heart valve to be fixed in its normal curved configuration.

It is another object of the invention to provide a method and apparatus for fixing a natural tissue heart valve that minimizes the number of adjustments that must be performed by human intervention.

It is another object of the invention to provide a method and apparatus for fixing a natural tissue heart valve that allows the valve leaflets to be fixed in an unstressed condition.

The invention, together with additional features and advantages thereof, may best be understood by reference to the following description taken in connection with the accompanying illustrative drawings. Throughout this description, like elements, wherever described, are referred to with like reference numbers.

BRIEF DESCRIPTION OF THE DRAWINGS

FIG. 5 is an exploded view of the outflow connector and cannula plug of the present invention around a tissue valve.

FIG. 6 is a side elevational view of the cannula plug and outflow connector of FIG. 5 in an assembled condition.

DESCRIPTION OF THE PREFERRED EMBODIMENT

Figure 1:
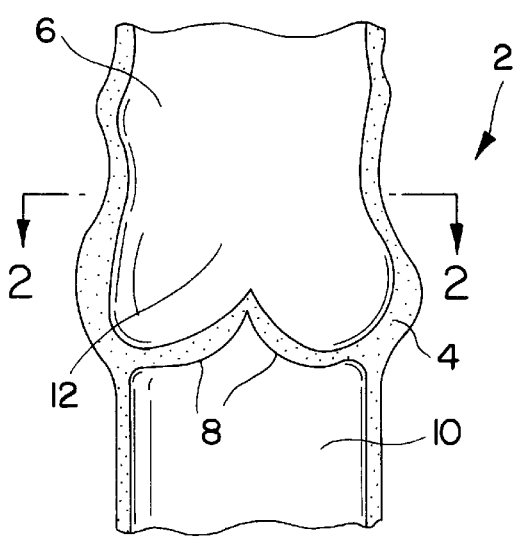
FIG. 1 is an axial cross-sectional view of a porcine aortic heart valve.
Figure 2:
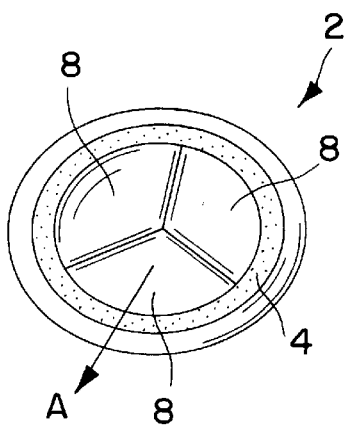
FIG. 2 is a cross-sectional view of the porcine valve of FIG. 1.
Figure 3:
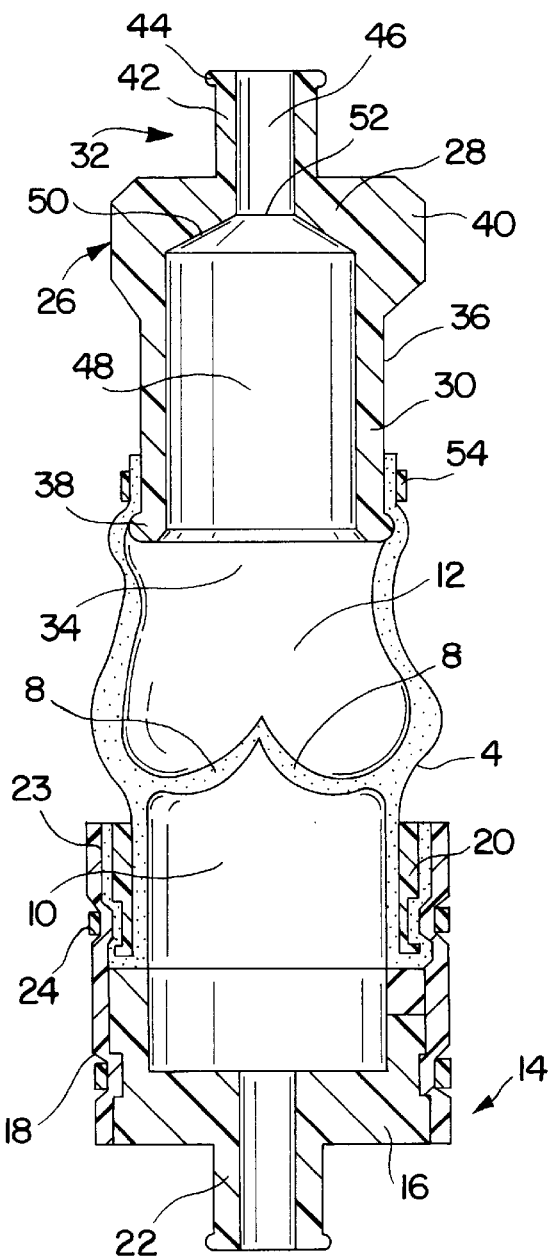
FIG. 3 is an axial, sectional view through a porcine aortic heart valve and associated prior art connectors.
Figure 4:
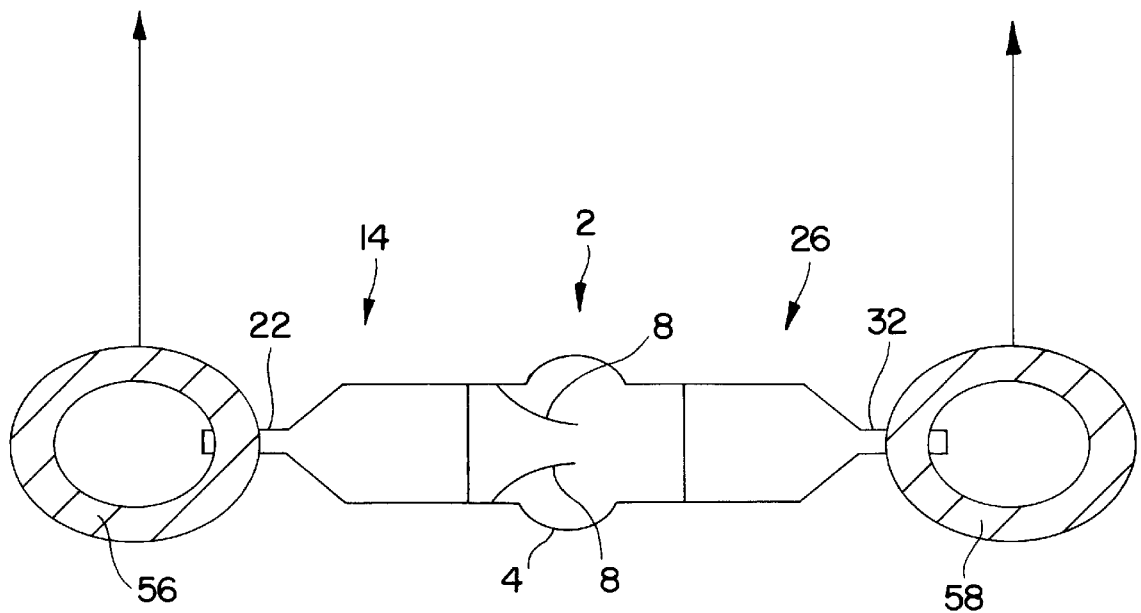
FIG. 4 is a schematic cross-sectional view of the heart valve and connectors of FIG. 3 attached to the manifolds of the prior art apparatus.

The present invention includes a device and method for fixing a natural tissue heart valve that meets the objects listed above. The device includes an outflow connector 26 and a cannula plug 60. FIG. 5 shows an exploded view of outflow connector, generally labeled 26, and cannula plug, generally labeled 60, in position around a heart valve 2.

Connector 26 referred to here is preferably identical to the outflow connector 26 described above.

Figure 12:
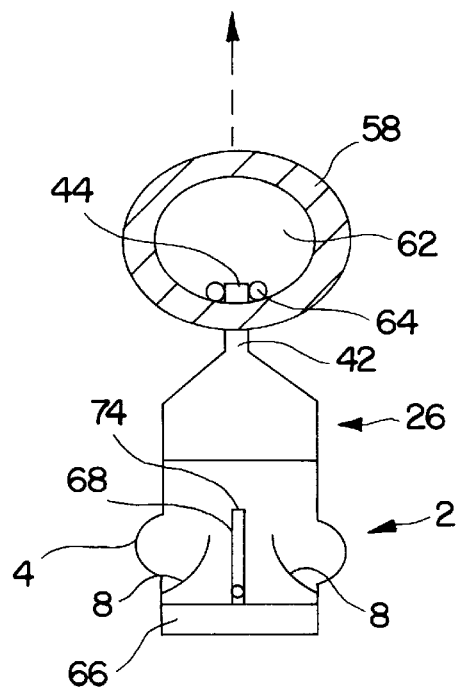
FIG. 12 is a schematic axial, sectional view through a porcine aortic heart valve in position on the fixture of the present invention.

Connector 26 connects valve 2 to a source of fluid $S_1$ and fluid pressure through manifold 58. FIG. 12 shows schematically a portion of manifold 58. Manifold 58 is hollow with an internal lumen 62 into which proximal rib 44 and neck 42 are placed. An annular seal or grommet 64 seals the opening around neck 42. Seal 64 is constructed of an elastomeric material that allows neck 42 to be forced into lumen 62. Seal 64 sealingly engages the exterior surface of neck 42. The depth of insertion of neck 42 through seal 64 can be varied as desired to accommodate valve-fixture assemblies of different overall lengths. As a result, it is only necessary to provide a valve-fixture assembly within certain length tolerances in order for it to be used in the invention. Proximal rib 44 resists any pull-out of neck 42 from manifold 58.

With this configuration, outflow section 12 is coupled to a source of fixative fluid $S_1$ that has a desired pressure $P_1$. Although different fixative fluids may be used, a glutaraldehyde solution is presently preferred as the source of fixative fluid.

As stated, the invention includes a cannula plug 60. As shown in FIGS. 5 and 7 through 10, cannula plug 60 includes a base 66 having a hollow base tube 68 attached thereto, a tube 70 and a ring 72. All the components of cannula plug 60, except tube 70, are preferably rigid and constructed of a rigid polymeric material, such as acetalphomopolymer or thermoplastic.

Figure 7:
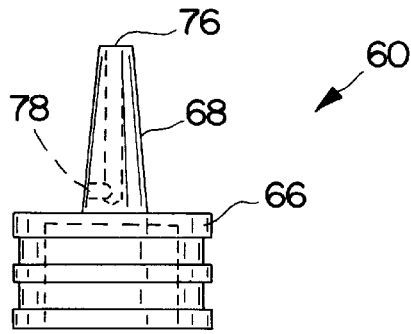
FIG. 7 is a side elevational view of the base of the cannula plug shown in FIG. 6.
Figure 8:
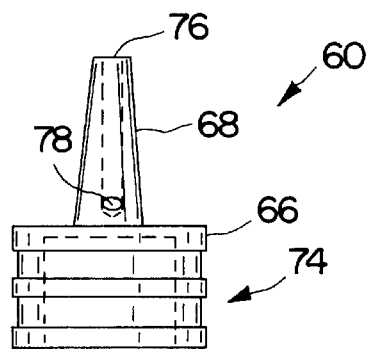
FIG. 8 is a side elevational view of the base of the cannula plug shown in FIG. 7 rotated 90° around the axis of the base tube.
Figure 9:
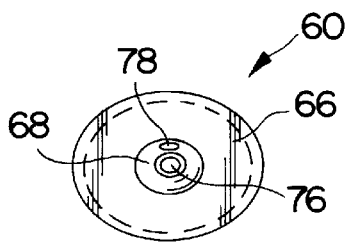
FIG. 9 is a plan view of the base of FIGS. 7 and 8.
Figure 10:
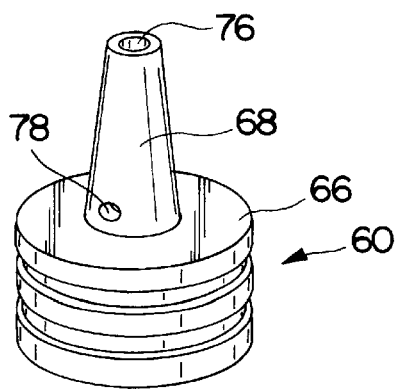
FIG. 10 is a perspective view of the base and base tube of the cannula plug of FIGS. 7 through 9.
Figure 11:
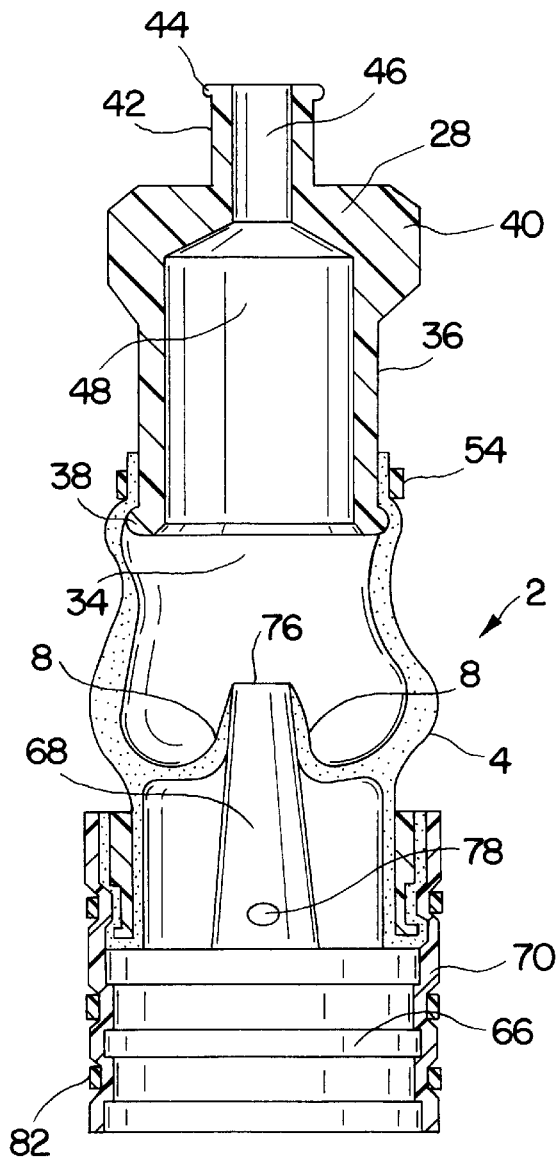
FIG. 11 is an axial, sectional view through a porcine heart valve and associated cannula plug and connector in position.

Base 66 is shown in detail in FIGS. 7 through 9. Base 66 is generally cylindrical and solid. A groove 74 extends around and into base 66. A hollow base tube 68 extends from the end of base 66. Hollow base tube 68 has an opening 76 at one end and an opening 78 near the connection of hollow base tube 68 to base 66. Openings 76 and 78 allow fluid to pass through hollow base tube 68 for a purpose to be described hereafter.

Tube 70 is substantially cylindrical in shape and is made of a thickness or material to be compliant. Tube 70 is preferably made of a compliant rubber material such as silicone rubber, although any durable, biocompatible compliant material may be used. Tube 70 comes in a variety of sizes corresponding to different sized valves 2 as will be explained hereafter.

Ring 72 also comes in a variety of sizes corresponding to various sizes of tubular wall 4 at the inflow section 10. A groove 80 extends into ring 72 at the distal end of ring 72.

In use, an appropriate sized ring 72 is chosen so that ring 72 will fit snugly around tubular wall 4 without pinching or folding the tissue of tubular wall 4. Ring 72 is then placed around inside tubular wall 4. Care must be taken to avoid trapping coronary arteries between ring 72 and tubular wall 4.

The tubular wall 4 of inflow section 10 is then folded over ring 72. The tissue of tubular wall 4 is pressed flat against the outer surface of ring 72 so that a cross-section of tubular wall 4, ring 72 and tubular wall 4 is presented radially outward from inflow section 10.

After ring 72 is in place, valve 2 is secured to ring 72 by tube 70. Tube 70 is placed over the tissue of tubular wall 4 that extends over ring 72. Tube 70 is secured to ring 72 by placing a tie wrap 82 around tube 70 at approximately the location of groove 80 on ring 72. Before securing tie wrap 82, it is important to verify that ring 72 closely approximates the shape of the annulus of tubular wall 4, that no annulus is exposed below ring 72 and that ring 72 does not restrict the stretching of the sinus area. Ring 72 may be rotated if necessary. Tie wrap 82 is then tightened into the recess formed by groove 80.

Base 66 is placed into the end of tube 70 opposite ring 72 so that tube 68 extends through leaflets 8 into outflow section 12. Base 66 is pushed into tube 70 so that base 66 is as close to the tissue of tubular wall 4 as possible without touching the tissue. Tube 70 is secured to base 66 by placing a tie wrap 82 around tube 70 at approximately the location of groove 74 in base 66. Tie wrap 84 is then tightened into groove 74 causing tube 70 to be moved into tight contact with base 66.

Valve 2 with outlet connector 26 and cannula plug 60 is placed in a reservoir of fixative fluid. Valve 2 must be completely immersed in the fixative fluid.

Outflow section 12 is subjected to fixative fluid under any desired fluid pressure $P_1$ from $S_1$ to create different differential fluid pressures across the tubular wall 4 of outflow section 12. Although these pressures can vary widely as described above, fluid pressure is transferred through base tube 68 from inflow section 10 to outflow section 12. Therefore, the fluid pressures in both inflow section 10 and outflow section 12 is about the same. This creates a zero differential fluid pressure across the leaflets 8.

During the time that fixative fluid under pressure $P_1$ is applied from source $S_1$ to the interior of valve 2, the exterior of valve 2 is also subjected to the action of a fixative fluid. This is preferably done by immersing valve 2 in a bath of fixative solution. In this configuration, the differential fluid pressure acting across tubular wall 4 of outflow section 12 is the difference between the atmospheric pressure from the bath and the internal pressure $P_1$ from source $S_1$.

In the preferred embodiment, the fluid pressure differential acting outwardly across tubular wall 4 is about 40 mm Hg. This is accomplished by immersing valve 2 in a bath of fixative fluid at atmospheric pressure and applying fixative fluid to the interior of valve 2 under pressure of about 40 mm Hg. With the invention, there is about a zero differential fluid pressure across the leaflets 8 and about a 40 mm Hg differential pressure acting outwardly across the tubular wall 4 of outflow section 12.

With fixative fluid under pressure $P_1$ applied to the interior of valve 2 and atmospheric pressure applied to the outside of valve 2, tubular wall 4 at outflow section 12 is expanded from its formerly shrunk or contracted condition and is fixed in the expanded condition. Valve leaflets 8 are fixed under zero differential pressure. In this condition, the collagen waveform of leaflets 8 is not adversely altered so that leaflets 8 are not adversely stiffened.

Although various sequences of operation can be employed, in a preferred sequence, each valve 2 is assembled with associated connector 26 and cannula plug 60 as described above. This valve-fixture assembly is then coupled to manifold 58. Next, valve 2, connector 26 and cannula plug 60 are immersed in a tank filled to an appropriate height with a glutaraldehyde fixative solution. Finally, fixative solution under pressure from source $S_1$ is introduced to the inflow sections 4 of valves 2 through manifold 58 and connector 26. Valves 2 are then subjected to the action of the fixative solution for a sufficient time to fix each valve 2 with the fixation occurring substantially simultaneously for all of valves 2. The length of time required will vary but may be, for example, about 24 hours to about 3 days.

This invention is applicable to the simultaneous fixation of a plurality of natural tissue heart valves 2. A preferred way to accomplish this is to connect a plurality of connectors 26 and cannula plugs 60 to valves 2 as described above. Each of the connectors 26 is connected to manifold 58 through a corresponding lumen 62 and seal 64 as described above. Valves 2 are then immersed in a bath of fixative fluid.

Although an exemplary embodiment of the invention has been shown and described, many changes, modifications and substitutions may be made by one having ordinary skill in the art without necessarily departing from the spirit and scope of this invention.

I claim:

1. A method of fixing a natural tissue heart valve having an interior, an exterior, a tubular wall having an outflow section, an inflow section and valve leaflets that allow fluid flow into the outflow section, the method comprising the steps of:

placing a hollow tube through the valve leaflets so that fluid pressure on a side of the valve leaflets is transferred to an opposite side of the valve leaflets through the tube;

subjecting the interior of the valve to a fixative fluid at a first pressure and the exterior of the valve to fixative fluid at a second pressure so that a first differential fluid pressure acts outwardly across the tubular wall of the outflow section and a second but unequal differential fluid pressure is formed across the valve leaflets.

2. The method as defined in claim 1 in which the first differential fluid pressure is greater than the second differential fluid pressure.

3. The method as defined in claim 1 in which the second differential fluid pressure is substantially zero.

4. The method as defined in claim 1 in which the first differential fluid pressure is sufficient to expand the tubular wall of the outflow section.

5. The method as defined in claim 4 in which the second differential fluid pressure is substantially zero.

6. The method as defined in claim 1 in which the first differential fluid pressure is in the range of from about 20 to about 50 mm of mercury and the second differential fluid pressure is no greater than about 4 mm of mercury.

7. The method as defined in claim 6 in which the second differential fluid pressure is substantially zero.

8. The method as defined in claim 1, in which the step of placing the hollow tube also includes the steps of attaching the hollow tube to a cannula plug and positioning the cannula plug in the inflow section of the valve so that the cannula plug prevents fluid in the inflow section of the valve from passing out of the inflow section of the valve past the cannula plug.

9. The method as defined in claim 1 further comprising the step of varying the second differential fluid pressure while subjecting the exterior of the valve to fixative fluid.

10. The method as defined in claim 1 further comprising the step of flowing fixative fluid through the valve leaflets.

11. A method of fixing a natural tissue heart valve having an interior, an exterior, a tubular wall defining a passage and valve leaflets dividing the passage into an inflow section leading to the leaflets and an outflow section leading away from the leaflets with the leaflets being openable to allow flow from the inflow section to the outflow section, the method comprising the steps of:

attaching a cannula plug to the inflow section to provide an inflow chamber with a first end wall having an inlet leading to the inflow chamber, the cannula plug having a base and a hollow tube connected to the base, the hollow tube having a first end and a second end, the first end of the hollow tube connected to the base, the hollow tube having a first hole near the first end to provide a fluid passage to the interior of the hollow tube, the hollow tube having a second hole near the second end;

attaching a fixture to the outflow section to provide an outflow chamber with a second end wall having an inlet leading to the outflow chamber;

subjecting the exterior of the valve to a fixative fluid; and flowing fixative fluid under pressure through the inlet into the outflow chamber, through the second hole in the hollow tube, through the hollow tube, out of the first hole and into the inflow chamber until the fixative fluid is present in both the inflow and outflow chambers and the pressure of the fixative fluid in the inflow and outflow chambers is equalized.

12. The method as defined in claim 11 in which the first fixture includes an end wall, a support ring and an elastomeric sleeve and the end wall is coupled to the support ring by the elastomeric sleeve and the step of attaching includes inserting the inflow section into the support ring.

13. The method as defined in claim 11 in which the first-mentioned step of attaching includes providing a support ring about the inflow section, folding tissue of the valve about an edge portion of support ring and clamping the folded tissue between an elastomeric sleeve and the support ring, and the first fixture includes an end wall coupled to the sleeve.

14. A method of fixing a natural tissue heart valve which includes a tubular wall defining a passage and valve leaflets dividing the passage into an inflow section leading to the leaflets and an outflow section leading away from the leaflets with the leaflets being openable to allow flow from the inflow section to the outflow section, the method comprising:

placing a hollow tube through the valve leaflets so that fluid pressure on a side of the valve leaflets is transferred to an opposite side of the valve leaflets through the tube;

coupling the inflow section to fixative fluid under pressure;

coupling the outflow section to fixative fluid under pressure;

immersing the valve in a bath of fixative solutions; and flowing fixative solution into the inflow section and the outflow section with the pressure of the fixative fluid in the outflow section being greater than the pressure of the bath acting on the valve to provide a first desired differential pressure acting outwardly across the tubular wall of the outflow section and with the pressure of the fixative fluid in the inflow chamber being sufficient in relation to the pressure of the fixative fluid in the outflow section to create a second desired differential pressure across the valve leaflets.

15. The method as defined in claim 14 in which the first desired differential fluid pressure acting outwardly across the tubular wall of the outflow section is greater than the second desired differential fluid pressure across the valve leaflets.

16. The method as defined in claim 15 in which the differential fluid pressure acting outwardly across the tubular wall of the outflow section is sufficient to enlarge the outflow section and the differential fluid pressure across the valve leaflets is no greater than about 4 mm of mercury.

17. The method as defined in claim 16 in which the differential fluid pressure across the valve leaflets is substantially zero.

18. The method as defined in claim 14 further comprising the step of flowing fixative fluid from the inflow section to the outflow section.

19. The method as defined in claim 14 in which the steps of coupling include coupling the inflow and outflow sections to first and second sources of fixative fluid, respectively.

* * * * *